US00PP26077P3

(12) United States Plant Patent
Pavlich

(10) Patent No.: US PP26,077 P3
(45) Date of Patent: Nov. 10, 2015

(54) ***SCABIOSA* PLANT NAMED 'VIVID IMAGINATION'**

(50) Latin Name: ***Scabiosa* spp.**
Varietal Denomination: Vivid Imagination

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 229 days.

(21) Appl. No.: 13/998,614

(22) Filed: Nov. 14, 2013

(65) Prior Publication Data

US 2015/0135388 P1 May 14, 2015

(51) Int. Cl.
*A01H 5/02* (2006.01)

(52) U.S. Cl.
USPC ..... Plt./478

(58) Field of Classification Search
USPC ..... Plt./478
See application file for complete search history.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A new and distinct *Scabiosa* plant named 'Vivid Imagination' characterized by strongly variegated leaves with lime green margins on green leaves, medium size violet flowers, a compact habit, and excellent vigor.

1 Drawing Sheet

Botanical designation: *Scabiosa* spp.
Variety denomination: 'Vivid Imagination'.
Parentage: Mutation of *Scabiosa* 'Vivid Violet'.

BACKGROUND OF THE INVENTION

The present invention relates to a new and distinct cultivar of *Scabiosa* plant given the name 'Vivid Imagination'. *Scabiosa* is in the family Dipsacaceae. This new cultivar originated from a whole plant mutation of *Scabiosa* 'Vivid Violet' found at the nursery in Canby, Oreg.

Compared to the mother plant, *Scabiosa* 'Vivid Violet' U.S. Plant Pat. No. 19,260, the new cultivar is variegated with the leaf margins lime rather than green. In addition the habit is more compact and the plant is less hardy.

Compared to *Scabiosa columbaria* 'Pink Lemonade', U.S. Plant Pat. No. 17,094, the new cultivar has violet rather than pink flower color and variegation occurs along the entire margin rather than mostly on the lobes.

SUMMARY OF THE INVENTION

*Scabiosa* 'Vivid Imagination' is uniquely characterized by strongly variegated leaves with lime green margins on green leaves, medium size violet flowers, a compact habit, and excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows five-month-old *Scabiosa* 'Vivid Imagination' in flower growing in 4" pots grown outside in full sun in early June in Canby, Oreg.

FIG. 2 shows six-month-old *Scabiosa* 'Vivid Imagination' growing in 4" pots grown outside in full sun in late June in Canby, Oreg.

DETAILED PLANT DESCRIPTION

The following is a detailed description of the new *Scabiosa* cultivar based on observations of an 18-month-old specimen grown in a half gallon container in a warm greenhouse in May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:
- *Type*.—Herbaceous perennial.
- *Hardiness*.—USDA Zone 8-10.
- *Size*.—43 cm wide and 26 cm tall to top of the foliage.
- *Form*.—Low mound.
- *Vigor*.—Excellent.

Stem:
- *Type*.—Rosettes which form a branching flowering stem.
- *Size*.—Grows to 17 cm long and 8 mm wide, branches of side rosettes grow to 10 cm long and 3.5 mm wide.
- *Internode length*.—Grows to 25 mm long.
- *Surface*.—Pubescent.
- *Color*.—Yellow Green 147B.

Leaf:

*Type*.—Simple.

*Arrangement*.—Opposite.

*Surface texture*.—Pubescent on both sides.

*Venation*.—Pinnate.

*Cauline leaves*.—Oblanceolate in outline, grow to 10 cm long and 3.5 cm wide, deeply pinnatifid with linear lobes and occasional secondary lobes, tips obtuse, bases clasping.

*Petiole base*.—Clasping.

*Color*.—Top side Green 137A with margins Yellow Green 145A, bottom side Yellow Green 147B with margins Yellow Green 146C.

*Petiole*.—10 mm long and 3 mm wide, Yellow Green 147B.

Inflorescence:

*Description*.—Long stalked, hemispherical, terminal heads, with outer florets larger than inner florets, flat topped.

*Mature size*.—Grows to 4 cm wide and 15 mm deep.

*Immature*.—Round, flat topped, 15 mm wide and 8 mm deep, Purple Violet N82C where buds just opening Purple Violet 77A, outside edge of closed buds Violet 84B on top half and White NN155A to Yellow Green 145C on bottom half.

*Peduncle*.—Grows to 22 cm tall and 2 mm wide, pubescent, Yellow Green 146B.

*Involucral bracts*.—10 to 15 in a single row, reflexed slightly and curled somewhat, linear-lanceolate, apex acute, margins entire, pubescent, 5 mm to 10 mm long and 1.5 mm to 4 mm wide, Yellow Green 146B on margins with centers Yellow Green 146B on buds to Yellow Green 146C on mature flowers.

*Fragrance*.—Slightly sweet.

*Lastingness of the flower heads*.—Approximately one week in summer and up to two weeks in cool weather.

Florets:

*Type*.—Perfect, zygomorphic.

*Number*.—Approximately 57 in number, 13 large outer florets, 13 mid size, and 37 small inner florets.

*Immature*.—Outer florets 7 mm long and 3.5 mm wide, tubular with the top rolled down, Violet 84B on top half and White NN155A to Yellow Green 145C on bottom half.

*Size*.—Largest florets grow to 20 mm long and 15 mm wide, tube 6 mm long and 1 mm wide and small florets are 7 mm long and 3 mm wide.

*Shape*.—Bilabiate with 5 lobes, terminal lobe the longest, and 2 to 3 small lower lobes; lobes obovate, revolute, tips obtuse, margins undulate.

*Surface texture*.—glabrous on top and pubescent on bottom.

*Color*.—Topside lobes and throat are Violet N88C; bottom side lobe outer edges N88C to inside lobes and lobe bases Violet Blue 91D; tube White NN155A.

*Calyx*.—Bristly, of 5 setae, 7 mm long, persistent, Greyed Purple 187A.

*Involucel*.—Persistent at the base of each flower, scarious, White 155D, campanulate, 1.5 mm deep and 1.5 mm wide, margins irregularly serrate.

*Pistil*.—17 cm long, ovary 2 mm long, Yellow Green 145C, pubescent, stigma and style 12 mm long, Violet 86D on top ⅓ to White NN155A on bottom ⅓.

*Stamen*.—4 in number, anthers 1.5 mm long, White 155D, pollen White 155D, filaments 1 mm long, Violet 86D.

Fruiting inflorescence: Persistence and showy.

*Shape*.—Conical.

*Size*.—17 mm long and 15 mm wide.

*Color*.—Clusters of showy seeds with the involucel, White 155A, and setae, Greyed Purple 187A, surrounding the seeds, Yellow Green 144A.

Seed: None viable.

*Fertility*.—Sterile.

Disease and pests: The new cultivar is typical to the genus. No known resistances to pests or diseases. No problems have been found in Canby, Oreg.

I claim:

1. A new and distinct *Scabiosa* plant as herein illustrated and described.

* * * * *

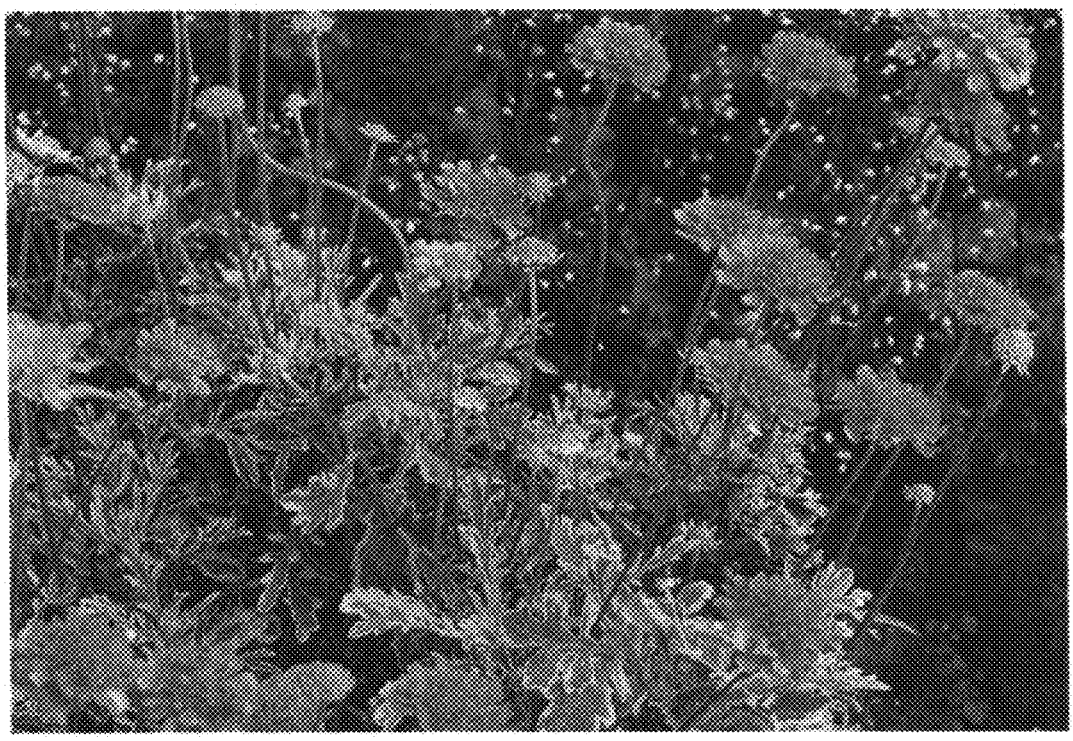

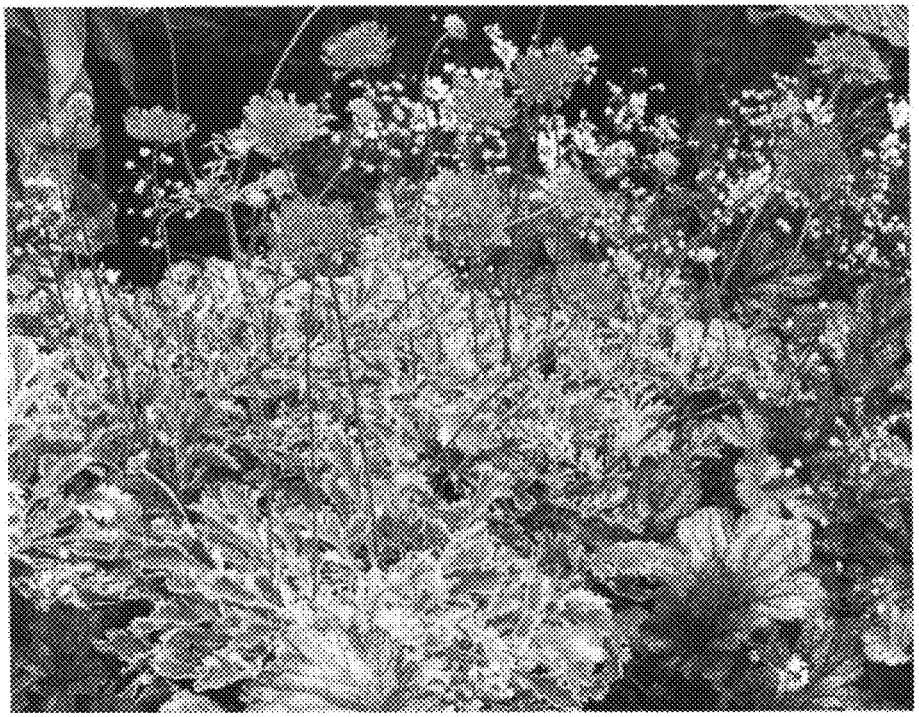
FIG. 1 above, FIG. 2 below